(12) United States Patent
Moine et al.

(10) Patent No.: US 9,320,804 B2
(45) Date of Patent: Apr. 26, 2016

(54) IMPLANTABLE BIO-RESORBABLE POLYMER

(75) Inventors: Laurence Moine, Saint-Cloud (FR); Laurent Bedouet, Paris (FR); Alexandre Laurent, Courbevoie (FR); Denis Labarre, Villebon (FR); Michel Wassef, Paris (FR); Van Nga Nguyen, Antony (FR)

(73) Assignees: OCCLUGEL, Jouy en Josas (FR); CENTRE NATIONAL DE LA RECHERCHE SCIENTIFIQUE (CNRS), Paris (FR); UNIVERSITE PARIS-SUD 11, Orsay (FR); ASSISTANCE PUBLIQUE—HOPITAUX DE PARIS, Paris (FR); UNIVERSITE PARIS DIDEROT PARIS 7, Paris (FR)

( * ) Notice: Subject to any disclaimer, the term of this patent is extended or adjusted under 35 U.S.C. 154(b) by 896 days.

(21) Appl. No.: 13/395,610

(22) PCT Filed: Sep. 9, 2010

(86) PCT No.: PCT/EP2010/063227
§ 371 (c)(1),
(2), (4) Date: May 24, 2012

(87) PCT Pub. No.: WO2011/029867
PCT Pub. Date: Mar. 17, 2011

(65) Prior Publication Data
US 2012/0230937 A1 Sep. 13, 2012

Related U.S. Application Data

(60) Provisional application No. 61/241,183, filed on Sep. 10, 2009.

(30) Foreign Application Priority Data

Sep. 10, 2009 (EP) ..................................... 09305830

(51) Int. Cl.
*A61K 47/34* (2006.01)
*A61K 47/48* (2006.01)
*C08F 290/06* (2006.01)
*C08L 55/00* (2006.01)

(52) U.S. Cl.
CPC ..... *A61K 47/48176* (2013.01); *A61K 47/48869* (2013.01); *C08F 290/061* (2013.01); *C08F 290/062* (2013.01); *C08L 55/005* (2013.01); *C08L 2205/02* (2013.01)

(58) Field of Classification Search
CPC .............. C08L 55/005; C08L 2666/24; C08L 2205/02; C08F 290/061; C08F 290/062; C08F 220/18
See application file for complete search history.

(56) References Cited

FOREIGN PATENT DOCUMENTS

| CN | 101265311 A | 9/2008 |
|---|---|---|
| JP | 2005330246 A | 12/2005 |
| WO | 2005/079856 A1 | 9/2005 |
| WO | 2006/045183 A1 | 5/2006 |
| WO | 2007/024323 A2 | 3/2007 |
| WO | 2009/132206 A1 | 10/2009 |

OTHER PUBLICATIONS

Peppas et al., J Cont. Release, 1999, 62, 81-87.*
Hongliang et al. Euro. Polymer J, 20005, 41, 948-57.*
Chitkara et al., Macromol. Biosci., 2006, 6, 977-990.*
Bedouet et al., Synthesis of hydrophilic intra-articular microspheres conjugated to ibuprofen and evaluation of anti-inflammatory activity on articular explants, Journal, Nov. 4, 2013, 11 pp., Elsevier B.V., France.
Archimed et al., Intra-articular fate of degradable poly(ethyleneglycol)-hydrogel microspheres as carriers for sustained drug delivery, Journal, Aug. 16, 2013, 9 pp. Elsevier B.V., France.
International Search Report mailed Oct. 14, 2010 (PCT/EP2010/063227); ISA/EP.
Saeed A O et al: "One-pot controlled synthesis of biodegradable and biocompatible co-polymer micelles" Journal of Materials Chemistry 2009 Royal Society of Chemistry GBR, vol. 19, No. 26, May 15, 2009, pp. 4529-4535.
Zhu J-L et al: "Novel polycationic micelles for drug delivery and gene transfer" Journal of Materials Chemistry 2008 Royal Society of Chemistry; Thomas Graham House; Science Park GB, vol. 18, No. 37, Aug. 6, 2008, pp. 4433-4441.
Yoo Hyuk Sang et al: "Biodegradable polymeric micelles composed of doxorubicin conjugated PLGA-PEG block copolymer" Journal of Controlled Release, Elsevier, Amsterdam, NL, vol. 70, No. 1-2, Jan. 29, 2001, pp. 63-70.
Osuga et al. (2002) J Vase Interv Radio/. 13:929-34.
Embocept® from Pharmacept literature (2005).
Commercial presentation: Quadrasphere®, Biosphere Medical (1996).
Spherex® from Pharmacia literature—Transarterial chemoembolization of liver metastases of colorectal carcinoma using degradable starch microspheres (Spherex): personal investigations and review of the literature (K. Wasser et al.—Der Radiologe, 2005, 45(7):633-43).
Spherex® from Pharmacia literature—Pharmacokinetic rationale for chemotherapeutic drugs combined with intraarterial degradable starch microsphere (spherex®) (CJ Johansson—Clinical pharmacokinetics, 1996, vol. 31, n° 3, pp. 231-240).
Spherex® from Pharmacia literature—Increased carboplatin concentration in liver tumors through temporary flow retardation with starch microspheres (Spherex) and gelatin powder (Gelfoam) (U. Pohlen et al—Journal of Surgical Research, vol. 92, Issue 2, Aug. 2000, pp. 165-170).

(Continued)

*Primary Examiner* — Kyle Purdy
(74) *Attorney, Agent, or Firm* — Banner & Witcoff, Ltd.

(57) ABSTRACT

The present invention relates to a polymer obtained from the polymerization of: (i) at least one monomer of formula (I) $(CH_2=CR_1)CO-K$ (I) wherein: K represents O-Z or NH-Z, Z representing $(CR_2R_3)_m-CH_3$, $(CH_2-CH_2-O)_m-H$, $(CH_2-CH_2-O)_m-CH_3$, $(CH_2)_m-NR_4R_5$ with m representing an integer from 1 to 30; $R_1$, $R_2$, $R_3$, $R_4$ and $R_5$ independently represent H or a C1-C6 alkyl; and (ii) at least one bio-resorbable block copolymer cross-linker.

9 Claims, No Drawings

(56) References Cited

OTHER PUBLICATIONS

Spherex® from Pharmacia literature—Biodegradable starch microspheres for cerebral arterial embolization (Laccourreye et al. Investigative Radiology, journals.lww.com, 1993).

Spherex® from Pharmacia literature—Induced hepatic arterial blockade by degradable starch microspheres in the rat (Nott et al—Nuclear Medicine Communications, 1987, journals.lww.com).

Spherex® from Pharmacia literature—The effect of different dose levels of degradable starch microspheres (Spherex®) on the distribution of a cytotoxic drug after regional administration to tumour-bearing rats (H. Teder et al—European Journal of Cancer, vol. 31, Issue 10, Sep. 1995, pp. 1701-1705).

Spherex® from Pharmacia literature—Chemoembolization of liver tumors (VX-2) using lyophilized Spherex (G. Berger et al—Zentralbl Chir., 1993, 118(3):140-4).

Spherex® from Pharmacia literature—Microwave coagulation therapy with stopping segemental hepatic blood flow by a balloon catheter and Spherex for a case with hepatic metastasis (T. et al.,—Acta Hepatologica Japonica, vol. 40, No. 11, pp. 626-630 (1999).

Spherex® from Pharmacia literature—Evaluation of efficient chemoembolization mixtures by magnetic resonance imaging therapy monitoring: an experimental study on the VX2 tumor in the rabbit liver (S. Pauser, et al—Cancer Research, Apr. 15, 1996, 56; 1863).

Bencherif et al., "End-group effects on the properties of PEG-co-PGA hydrogels," Acta Biomaterialia 5, 1872-83, 2009.

Moeinzadeh & Jabbari, "Mesoscale Simulation of the Effect of a Lactide Segment on the Nanostructure of Star Poly (ethylene glycol-co-lactide)-Acrylate Macromonomers in Aqueous Solution," J. Physical Chem. B 116, 1536-43, 2012.

Moeinzadeh et al., Gelation Characteristics and Osteogenic Differentiation of Stromal Cells in Inert Hydrolytically Degradable Micellar Polyethylene Glycol Hydrogels, Biomacromolecules 13, 2073-86, 2012.

Ward et al., "Effect of Monomer Type and Dangling End Size on Polymer Network Synthesis," J. Applied Polymer Science 89, 2506-19, 2003.

\* cited by examiner

IMPLANTABLE BIO-RESORBABLE POLYMER

CROSS-REFERENCE TO RELATED APPLICATIONS

The present application is a U.S. national phase filing of international application No. PCT/EP2010/063227 filed on Sep. 9, 2010, designating the United States of America and claiming priority to U.S. provisional patent application No. 61/241,183, filed on Sep. 10, 2009 and to European patent application No. 09305830.3 filed on Sep. 10, 2009. The present application claims priority to and the benefit of all the above-identified applications, and all the above-identified applications are incorporated by reference herein in their entireties.

FIELD OF THE INVENTION

The present invention relates to swellable and bio-resorbable cross-linked polymers liable to be implanted in an individual and optionally to deliver drugs to the individual.

TECHNICAL BACKGROUND

There is a need, in the field of biomaterial implantation, for resorbable and swellable particles. However, only incomplete solutions have been devised thus far.

Thus, gelatin sponges are biodegradable after implantation in tissues or injection in cavities, ducts or vessels. They can be impregnated with physiological saline and/or contrast media.

However, after their hydration they loose their shape and resistance. In addition, there is a great variability in resorption speed, which is influenced by many factors such as nature, homogeneity, size, enzymatic potential, and local inflammatory response. Moreover, since the mass of resorbable gelatin may vary in large proportions, the resorbtion time of the plug will consequently also take a variable time.

Another attempt consists of dextran starch microspheres (Spherex® from Pharmacia; Embocept® from Pharmacept) which have been devised to provide for resorbable implants. Indeed these dextran starch microspheres, which are non-toxic, are readily degradable and are notably used to provide temporary vascular occlusion, mainly for the treatment of tumor when co-administered with chemotherapeutic drugs.

However, dextran starch microspheres suffer from several limitations. First of all, these microsphers are available only in small sizes, with diameters below 100 μm. Such a small diameter does not allow targeted embolization, particularly for proximal occlusion. Besides, resorption is fast, with a usual half life below 1 hour, and cannot be accurately predicted since depends on the enzymatic capability to resorb a given microspheres volume.

Water-absorbent dry microspheres based on acrylic and PVA copolymers have also been proposed as swellable implants (Osuga et al. (2002) *J Vasc Intery Radiol.* 13:929-34). In a commercial presentation (Quadrasphere®, Biosphere Medical), these microspheres are under a dry form. For their use they are mixed with physiological saline, and/or iodinated contrast media. Compared to their initial size, their final size after water uptake varies according to the ionic charge of the medium (×2 or ×4 in saline and contrast medium respectively).

However the final size varies too much to allow for their controlled final volume after implantation, which is a serious limitation for their use. Besides, these microspheres are not resorbable.

It is therefore a goal of the present invention to solve the above problems.

SUMMARY OF THE INVENTION

The present invention arises from the unexpected finding, by the inventors, that the presence of neutral (meth)acrylates in a polymer cross-linked by bio-resorbable PLGA-, PEG- and/or PLA-based block copolymers can influence the rate of degradation of such a polymer while also allowing to control the swelling of the polymer. In addition, where the polymer is provided as a spherical particle, sphericity can be maintained even upon swelling.

Besides, it was further evidenced by the present inventors that in animal experiments performed in sheep shoulder joints, unlike microspheres of the prior art, polymer of the invention-based microspheres were quickly incorporated into the synovial tissue and that their residency time in synovium was at least of several weeks (1 month), making the microspheres of the invention suitable for delivering drug in the synovium for several weeks or months.

The present invention thus relates to a polymer obtained from the polymerization of:
(i) at least one monomer of formula (I)

wherein:
K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
$R_1$, $R_2$, $R_3$, $R_4$ and $R_5$ independently represent H or a C1-C6 alkyl; and
(ii) at least one bio-resorbable block copolymer cross-linker.

In an embodiment of the invention, the above-defined polymer is obtained from the polymerization of the at least one monomer, the at least one bio-resorbable block copolymer cross-linker, and at least one further monomer selected from the list comprising:
(i) a drug-carrying monomer of the following formula (III):

wherein:
$R_9$ represents H or a C1-C6 alkyl;
L represents a linker moiety having from 1 to 20 carbon atoms comprising a hydrolyzable function linked to the D group;
the D group represents a drug or a prodrug; and
(ii) a charged, ionisable, hydrophilic, or hydrophobic monomer of the following formula (V):

wherein:
$R_{11}$ represents H or a C1-C6 alkyl;
M represents a single bond or a linker moiety having from 1 to 20 carbon atoms;
F represents a charged, ionisable, hydrophilic, or hydrophobic group having 100 atoms at the most.
In another embodiment of the invention, the above-defined polymer is obtained from the polymerization of the at least one monomer, the at least one bio-resorbable block copolymer cross-linker, and the drug-carrying monomer.

In yet another embodiment of the invention, the above-defined polymer is obtained from the polymerization of the at least one monomer, the at least one bio-resorbable block copolymer cross-linker, and the at least one charged, ionisable, hydrophilic, or hydrophobic monomer.

These embodiments are advantageous in that where the polymer of the invention is polymerized from a drug-carrying monomer as defined above, the polymer can be used as a drug delivery system. Besides, where the polymer of the invention is polymerized from a charged, ionisable, hydrophilic, or hydrophobic monomer as defined above, the polymer may present with various physico-chemical surface characteristics enabling loading, i.e. non-covalently adsorbing, drugs to be delivered.

Thus, in a further embodiment of the invention, the above defined polymer is loaded with a drug or a prodrug.

In another embodiment of the invention, the above-defined polymer is obtained from the polymerization of the at least one monomer, the at least one block copolymer cross-linker, the at least one drug-carrying monomer, optionally the at least one charged, ionisable, hydrophilic, or hydrophobic monomer, and at least one hydrophilic monomer of the following formula (IV):

$$(CH_2=CR_{10})CO-Q \quad (IV)$$

wherein:
  $R_{10}$ represents H or a C1-C6 alkyl;
  Q represents a C1-C100 alkyl optionally substituted by at least one substituent selected from the group consisting of an hydroxyl, an oxo or an amino function.

The incorporation into the polymer of the invention of the above-defined hydrophilic monomer is advantageous in that it allows modulating the release of the drug by the polymer of the invention.

The present invention also relates to at least one polymer as defined above for use as a medicament.

The present invention also relates to a pharmaceutical composition comprising at least one polymer as defined above, in association with a pharmaceutically acceptable carrier.

DETAILED DESCRIPTION OF THE INVENTION

Bio-resorbable Block Copolymer

As intended herein, the expression "bio-resorbable" means that the block copolymer is degraded or cleaved when administered into a living organism, preferably a mammal, in particular a human, organism. As intended herein "bio-resorbable" indicates that the block copolymer may be hydrolyzed.

Preferably, the bio-resorbable block copolymer cross-linker as defined above is linear and presents ($CH_2$= ($CR_6$))— groups at both its extremities, wherein $R_6$ independently represents H or a C1-C6 alkyl. Preferably also, the bio-resorbable block copolymer cross-linker is a diblock or a triblock copolymer.

It also preferred that the block of the bio-resorbable block copolymer cross-linker as defined above is selected from the groups consisting of polyethylene glycol (PEG), poly-lactic acid (also named poly-lactide) (PLA), poly-glycolic acid (also named poly-glycolide) (PGA) and poly-lactic-glycolic acid (PLGA).

As is well known to one of skill in the art, PEG, PLA and PGA may be represented as follows, n representing their degree of polymerization:

PEG: [structure]

PLA: [structure]

PGA: [structure]

For PLGA which comprises both lactide and glycolide units, the degree of polymerizaton is the sum of the number of lactide and glycolide units.

More preferably, the bio-resorbable block copolymer cross-linker as defined above is of the following formula (II):

$$(CH_2=CR_7)CO-(X_n)_j-PEG_p-Y_k-CO-(CR_8=CH_2) \quad (II)$$

wherein:
  $R_7$ and $R_8$ independently represent H or a C1-C6 alkyl;
  X and Y independently represent PLA, PGA or PLGA;
  n, p, and k respectively represent the degree of polymerization of X, PEG, and Y, n and k independently being integers from 1 to 150, and p being an integer from 1 to 100;
  j represents 0 or 1.

Most preferably, the bio-resorbable block copolymer cross-linker as defined above is of a formula selected from the group consisting of:
$(CH_2=CR_7)CO-PLA_n-PEG-PLA_k-CO-(CR_8=CH_2)$,
$(CH_2=CR_7)CO-PGA_n-PEG_p-PGA_k-CO-(CR_8=CH_2)$,
$(CH_2=CR_7)CO-PLGA_n-PEG_p-PLGA_k-CO-(CR_8=CH_2)$,
$(CH_2=CR_7)CO-PEG_p-PLA_k-CO-(CR_8=CH_2)$,
$(CH_2=CR_7)CO-PEG_p-PGA_k-CO-(CR_8=CH_2)$, and
$(CH_2=CR_7)CO-PEG_p-PLGA_k-CO-(CR_8=CH_2)$;
wherein $R_7$, $R_8$, n, p and k are as defined above.

Polymer

As will be clear to one of skill in the art the polymer of the invention is a bio-resorbable (i.e. hydrolizable) cross-linked polymer. In particular the polymer of the invention is constituted of at least one chain of polymerized monomers as defined above, which at least one chain is cross-linked by bio-resorbable block copolymer cross-linkers as defined above.

Advantageously, the polymer of the invention is swellable, i.e. has the capacity to absorb liquids, in particular water.

As will also be clear to one of skill in the art, and by way of example, the monomers of the invention may also be represented as follows:

[chemical structures with labels K, D—L, F—M, Q and $R_1$, $R_9$, $R_{11}$, $R_{10}$]

Upon polymerization the monomers of the invention may then be represented as follows:

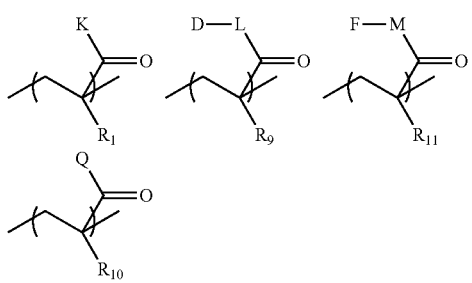

Preferably, the monomer of formula (I) as defined above is selected from the group consisting of sec-butyl acrylate, n-butyl acrylate, t-butyl acrylate, t-butyl methacrylate, methylmethacrylate, Ndimethyl-aminoethyl(methyl)acrylate, N,N-dimethylaminopropyl-(meth)acrylate, t-butylaminoethyl (methyl)acrylate, N,N-diethylaminoacrylate, acrylate terminated poly(ethylene oxide), methacrylate terminated poly (ethylene oxide), methoxy poly(ethylene oxide) methacrylate, butoxy poly(ethylene oxide)methacrylate, acrylate terminated poly(ethylene glycol), methacrylate terminated poly(ethylene glycol), methoxy poly(ethylene glycol)methacrylate, butoxy poly(ethylene glycol)methacrylate.

Most preferably, the monomer of formula (I) as defined above is poly(ethylene glycol) methyl ether methacrylate.

It is also preferred that the hydrophilic monomer as defined above is selected from the group consisting of (meth)acrylamide, 2-hydroxyethyl(meth)acrylate, N-vinyl-2-pyrrolidone, butyl(meth)acrylate, acrylic acid, acrylic anhydride, N-trishydroxymethyl methacrylamide, glycerol mono(meth) acrylate, hydroxypropyl(meth)acrylate, 4-hydroxybutyl (meth)acrylate.

Besides, it is preferred that F is selected from the group constituted of $COOH$, $COO^-$, $SO_3H$, $SO_3^-$, $PO_4 1H_2$, $PO_4 H^-$, $PO_4^{2-}$, $NR_{11}R_{12}$, $NR_{11}R_{12}R_{13}^+$, $R_{11}$, $R_{12}$ and $R_{13}$ independently representing H or a C1-C6 alkyl, a linear or branched alkyl group having from 1 to 20 carbon atoms, an aryl group having from 5 to 20 carbon atoms, a crown ether, and a cyclodextrin.

It is also preferred that L and M are of the following formula:

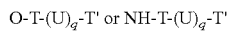

O-T-$(U)_q$-T' or NH-T-$(U)_q$-T' wherein T and T', identical or different, represent a C1-C6 alkyl chain optionally substituted by one or more hydroxyl, oxo, or amino group, U represents an hydrolysable function, such as an ester, amide, a disulfide, an amino-oxy or anhydride function, and q represents an integer from 0 to 2 for M and from 1 to 2 for L.

The polymer of the invention can be readily synthesized by numerous methods well-known to one of skill in the art. By way of example, the polymers of the invention can be obtained by suspension polymerization using either a direct or an inverse process as described below and in the Examples.

A direct suspension may proceed as follows: (a) stirring or agitating a mixture comprising (i) at least one monomer as defined above, and at least one bio-resorbable block copolymer cross-linker; (ii) a polymerization initiator present in amounts ranging from 0.1 to approximately 2 parts per weight per 100 parts by weight of the monomers; (iii) a surfactant in an amount no greater than about 5 parts by weight per 100 parts by weight of the monomers, preferably no greater than about 3 parts by weight and most preferably in the range of 0.5 to 1.5 parts by weight; and (iv) water to form an oil in water suspension; and (b) polymerizing the monomer(s) and the bio-resorbable block copolymer cross-linker.

An inverse suspension may proceed as follows: (a) stirring or agitating a mixture comprising: (i) at least one monomer as defined above, and at least one bio-resorbable block copolymer cross-linker; (ii) a polymerization initiator present in amounts ranging from 0.1 to approximately 2 parts per weight per 100 parts by weight of the monomers; (iii) a surfactant in an amount no greater than about 5 parts by weight per 100 parts by weight of the monomers, preferably no greater than about 3 parts by weight and most preferably in the range of 0.5 to 1.5 parts by weight; and (iv) oil to form a water in oil suspension; and (b) polymerizing the monomers and the bio-resorbable block copolymer cross-linker.

Drug

As intended here the drug or prodrug as defined above can be of any type and intended for the prevention or treatment of any disease or impairment.

Preferably, where a covalent interaction with the polymer of the invention is sought, the drug should be such that is carries a reactive function, such as a carboxyl, a hydroxyl, a thiol or an amino group. For instance, the drug may comprise an acidic functionality (propionic acid, carboxylic group, or an acetic acid carboxylic group) with a lipophilic tail composed by aryl derivatives As indicated above, in particular where the polymer of the invention is obtained from the polymerization at least one charged, ionisable, hydrophilic, or hydrophobic monomer, the drug may also be loaded onto the polymer, that is be adsorbed on the polymer by non-covalent interactions. No particular requirement are then imposed on the drug or prodrug to be loaded.

Loading may proceed by numerous methods well-known to one of skill in the art. For instance, the polymer in a dry form is made to swell in a solution containing a predetermined amount of the drug or the prodrug for 1 h to 24 h depending on the drug; the loaded polymer is then washed twice with a 0.9% (w/v) sodium chloride solution.

Besides, it is preferred that the drug as defined above is an anti-cancer drug or an NSAID.

Examples of suitable NSAIDs according to the invention encompass ibuprofen, ketoprofen, diclofenac, indomethacin or naproxen.

Examples of suitable anti-cancer drugs according to the invention encompass mitomycin, melphalan, methotrexate, raltirexed, gemcitabine, doxorubicine, or irinotecan.

Form of the Polymer

Preferably, the polymer of the invention is in the form of a film, a foam, a particle, a lump, a thread, or a sponge, and most preferably is in the form of a spherical particle. The spherical particle is preferably a microsphere, i.e. has a diameter upon swelling (i.e. upon hydration), ranging from 1 to 5000 μm, more preferably ranging from 100 to 600 μm.

In order to swell, the polymer of the invention may absorb, preferably in a controlled way, liquids, such as water, in particular from solutions commonly used in embolization procedures, such as physiological saline, glucose solution, plasma, ionic or non ionic iodinated contrast media, iron oxide based contrast media for magnetic resonance imaging, drug solutions, or any sterile apyrogen liquid that is injectable in the human or animal body. A defined and limited quantity of water is absorbed by the polymer of the invention, thereby enabling, where the polymer is a spherical particle, to anticipate the diameter upon swelling.

Pharmaceutical and Therapeutical Use of the Polymer

Advantageously, the range which may be obtained for the polymer of the invention in the form of spherical particles makes it particularly suitable to block arterioles that are detectable by angiography and accessible by navigation to catheter and micro-catheters. Besides, the ability of the polymer of the invention to absorb contrast media, such as barium sulphate, tungsten or tantalum, renders it particularly useful as a radio-opaque microsphere.

Advantageously also, resorption of the polymer of the invention depends on hydrolysis and not on an enzymatic mechanism. Resorption speed may thus be readily controlled by modulating the type and amount of bio-resorbable cross-linker and monomer as defined above.

Equally advantageous, resorption of the polymer of the invention may range from a few hours to a few weeks depending on the type and amount of bio-resorbable cross-linker and monomer as defined above. In addition, the polymer of the invention develops only a limited local inflammatory response upon implantation, since the degradation products of the polymer are non toxic and quickly eliminated.

Accordingly, the pharmaceutical composition as defined above is preferably for use as an implant, in particular for implantation into tissues, internal anatomical spaces, such as peritoneum and meningeal spaces, body cavities, ducts and vessels.

Besides, the pharmaceutical composition as defined above is preferably in an injectable form.

Preferably also, the pharmaceutical composition comprises the polymer of the invention in a dry form, such as a lyophilized form.

The pharmaceutical composition of the invention will be preferably used in the frame of embolization, in particular for uterine artery embolization (UAE), or for haemostasis. In embolization, the polymer of the invention need not comprise drugs or be loaded with drugs.

The pharmaceutical composition of the invention is also preferably used for treating cancer. In this case, treatment may occur by embolization, in particular by repeated embolization, and/or by delivery of anti-cancer drugs or predrugs comprised in the polymer of the invention or loaded on the polymer of the invention.

Besides, the pharmaceutical composition of the invention may be preferably used for preventing or treating inflammation. In this case, it is preferred that the polymer of the invention comprises NSAIDs or be loaded by NSAIDs. In particular, the pharmaceutical composition of the invention is particularly suited for preventing or treating inflammation associated with:
   joints cavities, tendons, cartilage, and bone defects;
   operative cavities after surgery of brain, in maxillar bone after teeth extraction, in bone after resections, in liver or kidney after surgical tumor resection;
   muscles, in particular in cases of myositis or rupture;
   cerebrospinal fluid cavities in the central nervous system;
   joint surgery, arthroscopy, intrarticular lavage, menisectomy, osteotomy.

EXAMPLES

Example 1

1. Synthesis of the Bio-Resorbable Cross-linker by the HEMA/PEGMA Method:
1.1. PLA
First Step:
   In a dry schlenk containing a magnetic stirring bar, lactide (2.2232 g; 0.0154 mol) and hydroxyethyl methacrylate (0.75 mL; 0.0062 mol) were dissolved in 5 ml of toluene under nitrogen. The reaction was initiated by introducing a toluene solution of $Sn(Oct)_2$ (8 mg) into the above system. After 20 h at 90° C., 5 ml of chloroform was added to dilute the reaction mixture and the formed polymer was purified by precipitating in a large volume of petroleum ether. Yield 94%.
   Characterization by $^1H$ NMR in $CD_3COCD_3$: 1.53 (m, $CH_3$, PLA), 1.91 (s, $CH_3$, methacrylate), 4.38 (m, $CH_2$, HEMA), 5.17 (m, CH, PLA), 5.65-6.10 (m, $CH_2$=C)
Second Step:
   The polymer formed in the first step was further modified through the hydroxyl group at the end of PLA chain by reacting with methacryloyl chloride. The preformed polymer (1.07 mmol of OH group, 1 eq.) was dissolved in anhydrous $CH_2Cl_2$ (2.5 ml) in a three necked flask equipped with magnetic stirrer and a dropping funnel. The content of the flask was cooled to 0° C. and triethylamine (1.5 eq.; 0.0016 mol) was added. The solution was stirred and then methacryloyl chloride (1.5 eq.; 0.0016 mol) in $CH_2Cl_2$ (2.5 ml) was added dropwise to the solution. The stirring was continued 1 h at 0° C. and then one night at room temperature. The triethylamine salt was removed by filtration and the polymer was precipitated in a large volume of petroleum ether. Yield: 95%.
   Characterization by $^1H$ NMR in $CD_3COCD_3$: 1.53 (m, $CH_3$, PLA), 1.91 (m, $CH_3$, methacrylate), 4.39 (m, $CH_2$, HEMA), 5.17 (m, CH, PLA), 5.65-6.16 (m, $CH_2$=C)
1.2. PGA
First Step:
   In a dry schlenk containing a magnetic stirring bar, glycolide (0.6 g; 0.005 mol) and hydroxyethyl methacrylate (21 mg; 0.0016 mol) were dissolved in 2 ml of toluene under nitrogen. The reaction was initiated by introducing a toluene solution of $Sn(Oct)_2$ (5 mg) into the above system. After 20 h at 90° C., 5 ml of chloroform was added to dilute the reaction mixture and the formed polymer was purified by precipitating in a large volume of petroleum ether. Yield 96%.
   Characterization by $^1H$ NMR in $CD_3COCD_3$: 1.91 (s, $CH_3$, methacrylate), 4.38 (m, $CH_2$, HEMA), 4.80 (m, $CH_2$, PGA), 5.65-6.09 (s, $CH_2$=C)
Second Step:
   The polymer formed in the first step was further modified through the hydroxyl group at the end of PGA chain by reacting with methacryloyl chloride. The preformed polymer (1 mmol of OH group, 1 eq.) was dissolved in anhydrous $CH_2Cl_2$ (2 ml) in a three necked flask equipped with magnetic stirrer and a dropping funnel. The content of the flask was cooled to 0° C. and triethylamine (1.5 eq.; 0.0015 mol) was added. The solution was stirred and then methacryloyl chloride (1.5 eq.; 0.0015 mol) in $CH_2Cl_2$ (2 ml) was added dropwise to the solution. The stirring was continued 1 h at 0° C. and then one night at room temperature. The triethylamine salt was removed by filtration and the polymer was precipitated in a large volume of petroleum ether. Yield: 50%.
   Characterization by $^1H$ NMR in $CD_3COCD_3$: 1.90 (m, $CH_3$, methacrylates), 4.40 (m, $CH_2$, HEMA), 4.81 (m, $CH_2$, PGA), 5.65-6.16 (m, $CH_2$=C)

1.3. PLGA

First Step:

In a dry schlenk containing a magnetic stirring bar, lactide (1.18 g; 8.23 mmol), glycolide (0.95 g; 8.23 mmol) and hydroxyethyl methacrylate (0.53 g; 4.1 mmol) were dissolved in 5 ml of toluene under nitrogen. The reaction was initiated by introducing a toluene solution of $Sn(Oct)_2$ (8 mg) into the above system. After 20 h at 90° C., 5 ml of chloroform was added to dilute the reaction mixture and the formed polymer was purified by precipitating in a large volume of petroleum ether.

Characterization by $^1$H NMR in $CD_3COCD_3$: 1.49 (m, $CH_3$, PLA), 1.92 (s, $CH_3$, methacrylate), 4.44 (m, $CH_2$, HEMA), 4.83 (m, $CH_2$, PGA), 5.25 (m, CH, PLA), 5.65-6.10 (s, $CH_2$=C)

Second Step:

The polymer formed in the first step was further modified through the hydroxyl group at the end of PLGA chain by reacting with methacryloyl chloride. In a typical reaction, the preformed polymer (8.23 mmol of OH group, 1 eq.) was dissolved in anhydrous $CH_2Cl_2$ (20 ml) in a three necked flask equipped with magnetic stirrer and a dropping funnel. The content of the flask was cooled to 0° C. and triethylamine (1.5 eq.; 12.34 mmol) was added. The solution was stirred and then methacryloyl chloride (1.5 eq.; 12.34 mmol) in $CH_2Cl_2$ (10 ml) was added dropwise to the solution. The stirring was continued 1 h at 0° C. and then one night at room temperature. The triethylamine salt was removed by filtration and the polymer was precipitated in a large volume of petroleum ether.

Characterization by $^1$H NMR in $CD_3COCD_3$: 1.51 (m, CH3, PLA), 1.92 (s, CH3, methacrylates), 4.44 (m, CH2, HEMA), 4.83 (m, CH2, PGA), 5.25 (m, CH, PLA), 5.65-6.16 (m, CH2=C)

Synthesis reactions are summarized in the following scheme:

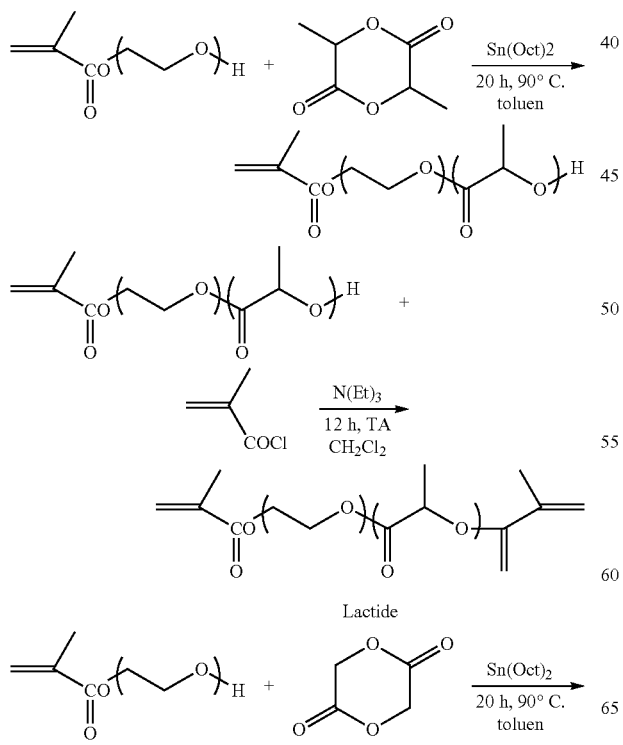

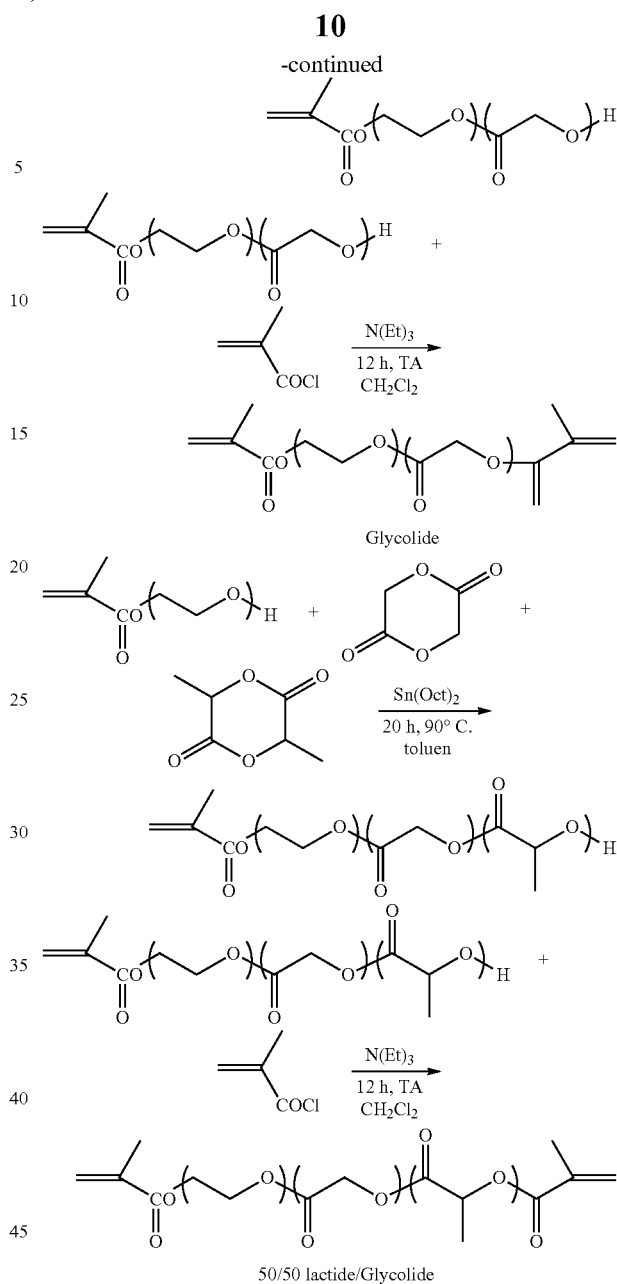

50/50 lactide/Glycolide

2. Synthesis of the Bio-resorbable Cross-linker by the PEG Method:

2.1. PLA with TEG (PEG n=4)

First Step:

In a dry schlenk containing a magnetic stirring bar, the tetraethyleneglycol (0.139 g; 0.0007 mol) was reacted with d,l-lactide (1.032 g; 0.0072 mol) for 20 h at 115° C. using stannous octoate as catalyst (5 mg) under nitrogen. Then, the polymer was dissolved in chloroform, precipitated in a large volume of petroleum ether.

Characterization by $^1$H NMR in $CD_3COCD_3$: 1.54 (m, $CH_3$, PLA), 3.64 (m, $CH_2$, PEG), 4.26 (m, $CH_2$, PEG), 5.16 (m, CH, PLA)

Second Step:

The polymer formed in the first step was further modified through the hydroxyl groups at the end of PLA chNSAID by reacting with methacryloyl chloride. In a typical reaction, the preformed polymer was dissolved in anhydrous $CH_2Cl_2$ (10 ml) in a three necked flask equipped with magnetic stirrer and a dropping funnel. The content of the flask was cooled to 0° C. and triethylamine (1.5 eq.; 0.0018 mol) was added. The solution was stirred and then methacryloyl chloride (1.5 eq.; 0.0018 mol) in CH$_2$Cl$_2$ (5 ml) was added dropwise to the solution. The stirring was continued 1 h at 0° C. and then one night at room temperature. The triethylamine salt was removed by filtration and the polymer was precipitated in a large volume of petroleum ether.

Characterization by $^1$H NMR in CD$_3$COCD$_3$: 1.56 (m, CH$_3$, PLA), 1.97 (m, CH$_3$, methacrylate), 3.65 (m, CH$_2$, PEG), 4.29 (m, CH$_2$, PEG), 5.17 (m, CH, PLA), 5.64-6.20 (m, CH$_2$=C).

2.2. PLGA with PEG 1500 (n=34)
First Step:

In a dry schlenk containing a magnetic stirring bar, the PEG1500 (2.25 g; 0.0015 mol) was reacted with d,l-lactide (0.865 g; 0.006 mol) and glycolide (0.697 g; 0.006 mol) for 20 h at 115° C. using stannous octoate as catalyst (10 mg) under nitrogen. Then, the polymer was dissolved in chloroform, precipitated in a large volume of petroleum ether.

Characterization by $^1$H NMR in CD$_3$COCD$_3$: 1.55 (m, CH$_3$, PLA), 3.64 (m, CH$_2$, PEG), 4.25 (m, CH$_2$, PEG), 4.84 (m, CH$_2$, PGA), 5.20 (m, CH, PLA)

Second Step:

The polymer formed in the first step was further modified through the hydroxyl groups at the end of PLA chNSAID by reacting with methacryloyl chloride. In a typical reaction, the preformed polymer was dissolved in anhydrous CH$_2$Cl$_2$ (20 ml) in a three necked flask equipped with magnetic stirrer and a dropping funnel. The content of the flask was cooled to 0° C. and triethylamine (1.5 eq.; 0.0045 mol) was added. The solution was stirred and then methacryloyl chloride (1.5 eq.; 0.0045 mol) was added dropwise to the solution. The stirring was continued 1 h at 0° C. and then one night at room temperature. The triethylamine salt was removed by filtration and the polymer was precipitated in a large volume of petroleum ether/diethylether.

Characterization by $^1$H NMR in CD$_3$COCD$_3$: 1.56 (m, CH$_3$, PLA), 1.94 (m, CH$_3$, methacrylate), 3.63 (m, CH$_2$, PEG), 4.29 (m, CH$_2$, PEG), 4.86 (m, CH$_2$, PGA), 5.23 (m, CH, PLA), 5.64-6.15 (m, CH$_2$=C)

Synthesis reactions are summarized in the following scheme:

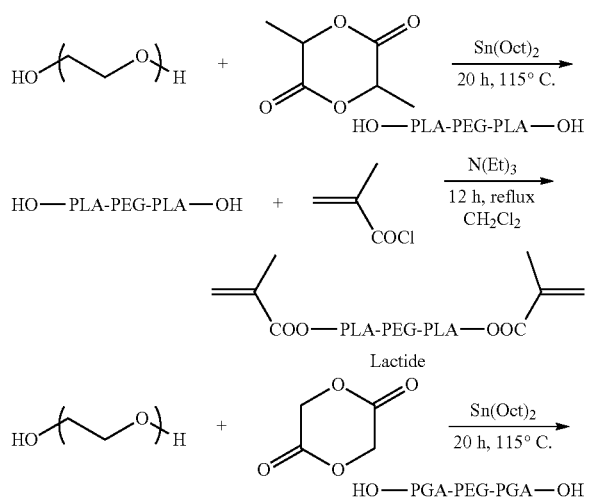

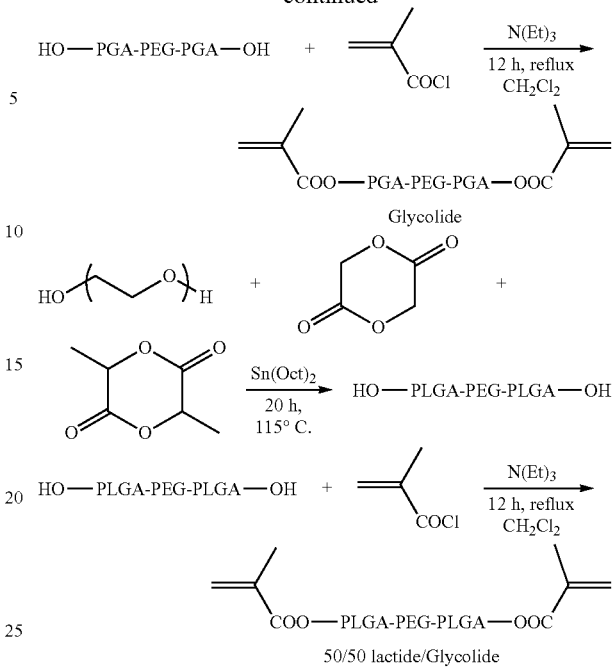

50/50 lactide/Glycolide

3. Synthesis of the Microspheres by Suspension Polymerization:

3.1. With the PLA Cross-Linker from the HEMA/PEGMA Method

A 0.5% of aqueous solution of 88% hydrolyzed polyvinylalcohol (90 ml) was introduced into a 100 ml reactor and allowed to stand under a nitrogen atmosphere for 15 min. The monomer phase containing poly(ethylene glycol)methyl ether methacrylate (2.77 g), PLA cross-linker (0.7 g) and 1 wt % AIBN solubilized in 4.3 ml of xylene was degassed by bubbling nitrogen through the solution for 15 min. The monomer phase was added to the aqueous phase at 50° C. and agitated by means of a propeller type stirrer at an appropriate velocity so as to obtain monomer droplets of desired diameter. The temperature was increased to 80° C. and stirred for 5 h. The mixture was filtered hot and washed with water and acetone. Then, beads were freeze dry. Size 390±100 µm.

3.2. With the PLGA Cross-linker from the HEMA/PEGMA Method

A 0.75% of aqueous solution of 88% hydrolyzed polyvinylalcohol (220 ml) was introduced into a 1000 ml reactor and allowed to stand under a nitrogen atmosphere for 15 min. The monomer phase containing poly(ethylene glycol) methyl ether methacrylate (5.9 g; 19.6 mmol), PLGA cross-linker (1 g; 1.7 mmol) and 1 wt % AIBN solubilized in 10 ml of toluene was degassed by bubbling nitrogen through the solution for 15 min. The monomer phase was added to the aqueous phase at 50° C. and agitated by means of a propeller type stirrer at an appropriate velocity so as to obtain monomer droplets of desired diameter. The temperature was increased to 80° C. and stirred for 5 h. The mixture was filtered hot and washed with water and acetone. Then, beads were freeze dry. Size=246±150 µm.

3.3. With the PLA Cross-linker from PEG Method

A 0.5% of aqueous solution of 88% hydrolyzed polyvinylalcohol (90 ml) was introduced into a 100 ml reactor and allowed to stand under a nitrogen atmosphere for 15 min. The monomer phase containing poly(ethylene glycol) methyl ether methacrylate (3.252 g), PLA cross-linker (0.36 g) and 1 wt % AIBN solubilized in 4.3 ml of xylene was degassed by bubbling nitrogen through the solution for 15 min. The monomer phase was added to the aqueous phase at 50° C. and agitated by means of a propeller type stirrer at an appropriate velocity so as to obtain monomer droplets of desired diameter. The temperature was increased to 80° C. and stirred for 5 h. The mixture was filtered hot and washed with water and acetone. Then, beads were freeze dry. Size 450±100 µm.

Synthesis reactions are summarized in the following scheme:

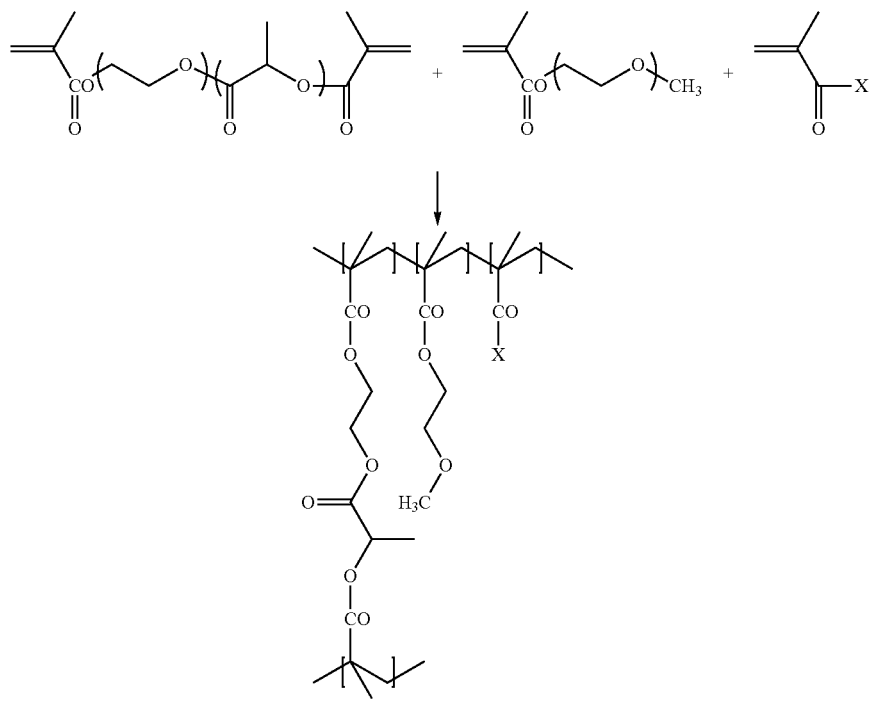

4. Degradation Analysis:

50 mg of dried microspheres were weighed and immersed in 10 ml of PBS solution in individual vials kept at 37° C. or 70° C. Samples were removed at designed times and immediately freezed to stop the degradation process. 6 samples were removed at each time point to gauge the variability in the degrading samples. The pH of each sample solution was measured and the mechanical properties of microspheres were determined using a compression method with a TAX-T2 apparatus. The results are presented in the following table.

| Microspheres | Cross-linker | Size (µm) | Degradation time (days) |
|---|---|---|---|
| P1 | HEMA-PGA (4%) | 100-300 | 8 |
| P2 | HEMA-PLGA (4%) | 300-500 | 35 |
| P3 | HEMA-PLGA (4%) | 100-300 | 14 |
| P4 | HEMA-PLGA (6%) | 100-300 | 28 |

5. Mechanical Properties

Rigidity and elasticity are dominant parameters for injectability and repartition of embolization microsphere in a given vascular network.

As illustrated in the following table, the microspheres of the invention, upon swelling in an appropriate medium, such as such as saline, glucose solution, contrast media and mixtures of them, present mechanical performances of rigidity and elasticity which are adapted to the technical conditions of embolization and which compare to current commercialized microspheres: rigid to resist to the compression during the injection in syringes and catheters (microcatheters with an internal diameter mini 0.7 mm) and an elastic to regain its shape quickly after a deformation.

|  | Embosphere ® | Embozene ® | Hepasphere ® | Microspheres of the invention (P2) |
|---|---|---|---|---|
| Young modulus (MPa) | 3.79 ± 0.6 | 1.93 ± 0.8 | 2.6 | 3.64 ± 0.87 |
| Yield strength (MPa) | 1.28 ± 0.4 | 0.1 ± 0.06 | 0.22 ± 0.13 | 0.33 ± 0.18 |

6—In vivo

Microspheres prepared as indicated above (P1, cross-linker HEMA-PGA, 200 µm, 2 g sterilised, size 100-300 µm) were sterilized at 120° C. 20 min and were suspended in a mixture of saline and iodinated contrast medium (250 mg in 4 ml) and injected by a 1 mL syringe slowly in the renal flow with a microcatheter which tip was prealably positioned in the ostium of renal arteries in a pig. There was no blockade of the microcatheter and no resistance during manual injection of the microspheres suspension. At the end of embolisation an occlusion of the arteries in the embolised segment was observed on the angiographic control. Animal was sacrificed at 48H and kidneys sampled. Under pathologic microscopical examination, microspheres were visible in kidneys. They occluded completely the vessel lumens of several interlobular arteries. They looked as clear spheres. Some inflammatory cells were present on the microspheres. A partial resorption (~50%) is clearly visible (presence of vacuoles).

Example 2

1. Synthesis of Ibuprofen Monomers:
1.1. HEMA-iBu:
The following reaction was performed:

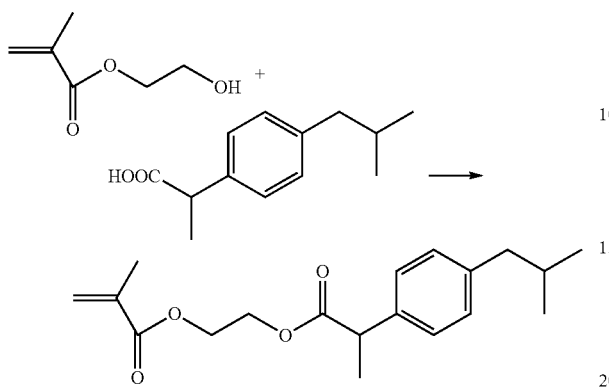

In a round bottom flask containing a magnetic stirring bar, ibuprofen (0.34 g; 1.65 mmol) and 4-Dimethylaminopyridine (0.01 g; 0.09 mmol) were solubilized in dry $CH_2Cl_2$ (4 ml) under nitrogen atmosphere. Hydroxyethyl methacrylate (0.21 g; 1.65 mmol) and a mixture of dicyclohexylcarbodiimide (0.34 g; 1.65 mmol) dissolved in 2 ml of dry $CH_2Cl_2$ were sequentially added at 0° C. After reacting 24 h at 0° C., the mixture was filtrate and the crude product was purified on silica gel column (cyclohexane/ethyl acetate: 2/1).

Characterization by $^1H$ NMR in $CD_3COCD_3$: 0.88 (d, $CH_3$, isopropyl), 1.43 (d, $CH_3$—CH, ibuprofen), 1.85 (m, $CH_3$, methacrylate +CH-iPr, ibuprofen), 2.44 (d, $CH_2$-phenyl, ibuprofen), 3.75 (q, phenyl-CH—COO—, ibuprofen), 4.31 (m, $CH_2$, HEMA), 5.59-5.98 (m, $CH_2$=C), 7.16 (dd, $C_6H_4$)

1.2. GMA-iBu
The following reaction was performed:

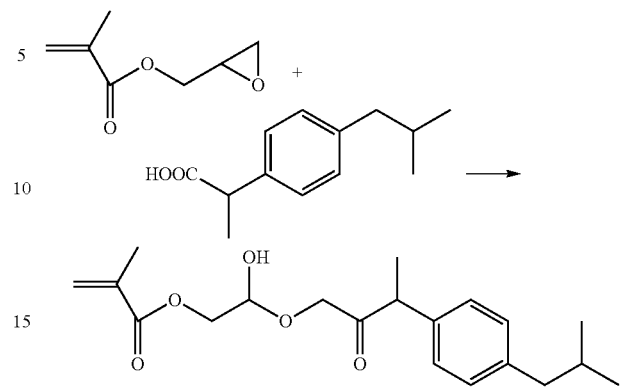

Glycidyl methacrylate (1.348 g; 9.5 mmol), ibuprofen (1.955 g; 9.5 mmol), hydroquinone (0.2 g) and pyridine (2 ml) were dissolved in 5 ml of DMF. The mixture was shaken under vacuum at 40° C. for 6 h. Then, the mixture was cooled and poured in aqueous saturated $NaHCO_3$ solution (20 ml). The organic phase was extracted three times by ethyl acetate, washed with saturated NaCl solution, dried on $MgSO_4$ and the solvent evaporated under reduced pressure. The residue was purified by chromatography (ethyl acetate/cyclohexane: 1/5). Yield: 40%.

Characterization by $^1H$ NMR in $CDCl_3$: 0.89 (d, $CH_3$, isopropyl), 1.51 (d, $CH_3$—CH, ibuprofen), 1.85 (m, CH-iPr, ibuprofen), 1.94 (s, $CH_3$, methacrylate), 2.45 (d, $CH_2$-phenyl, ibuprofen), 3.75 (q, phenyl-CH—COO—, ibuprofen), 4.08-4.19 (m, $CH_2$—CH(OH)—$CH_2$), 5.60-6.12 (m, $CH_2$=C), 7.16 (dd, $C_6H_4$)

2. Synthesis of Microspheres by Suspension Polymerization:
The following reaction was performed:

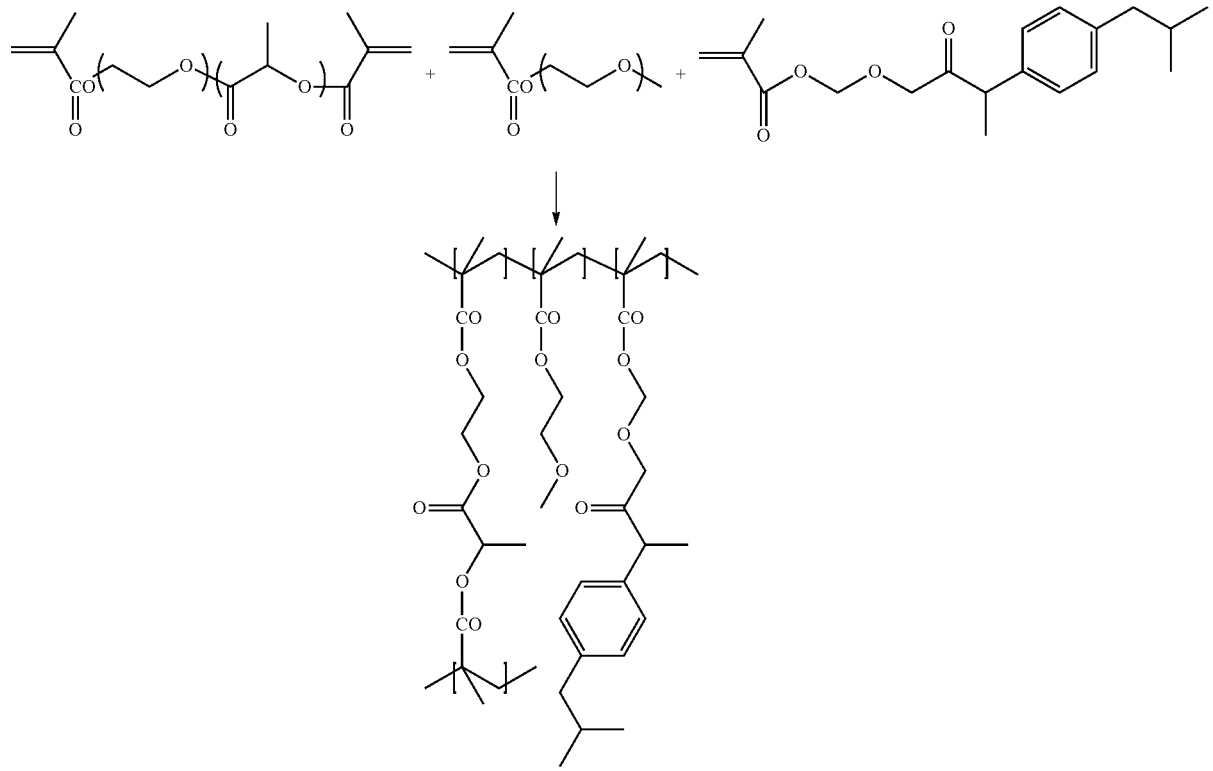

A 0.75% of aqueous solution of 88% hydrolyzed polyvinylalcohol (220 ml) was introduced into a 1000 ml reactor and allowed to stand under a nitrogen atmosphere for 15 min. The monomer phase containing HEMA-iBu (1.6 g; 5 mmol), poly(ethylene glycol)methyl ether methacrylate (5.9 g; 19.6 mmol), PLGA cross-linker (1 g; 1.7 mmol) and 1 wt % AIBN solubilized in 10 ml of toluene was degassed by bubbling nitrogen through the solution for 15 min. The monomer phase was added to the aqueous phase at 50° C. and agitated by means of a propeller type stirrer at an appropriate velocity so as to obtain monomer droplets of desired diameter. The temperature was increased to 80° C. and stirred for 5 h. The mixture was filtered hot and washed with water and acetone. Then, beads were freeze dry.

The characteristics of the prepared microspheres are summarized in the following table:

| Microspheres | Cross-linker | iBu | size |
| --- | --- | --- | --- |
| P5 | HEMA-PLGA(8%) | 20 | 40-100 |
| P6 | TEG-PLGA (5%) | 20 | 40-100 |
| P7 | TEG-PLGA (3%) | 43 | 40-100 |

3. In vitro Release of Ibuprofen:

220 mg of ibuprofen loaded microspheres (P6) was suspended in a vial containing 30 ml of PBS (pH7.4). The vial was incubated at 37 ° C. with constant shaking. At time intervals, the vial was centrifugated for 10 s and sample (100 µl) from the releasing medium was withdrawn for UV and HPLC analyses. The withdraw volume was replaced with fresh buffer followed by resuspending before continuing incubation.

| | % iBu released | | |
| --- | --- | --- | --- |
| Microspheres | Day 30 | Day 60 | Day 90 |
| P6 TEG-PLGA (5%)-20% iBu | 6 | 8 | 14 |
| P7 TEG-PLGA (3%) 43% iBu | 1 | 1.5 | 2 |

4. In vivo: Intra-Articular Injection of Microspheres (P8+P9) in Sheep Joint Shoulder An implantation study of microspheres was performed in sheep shoulder joints (gleno-humeral joint). Two species of microspheres (40-100 µm) were injected: resorbable micospheres (P8-TEG-PLGA 6% with PEGMMA 300) and non-resorbable microspheres (P9-PEGdiacrylate (M=575) 6% with PEGMMA 300) which are inflammatory. One week and one month after intra-articular injection, the synovial inflammatory reaction induced by resorbable microspheres was compared to inflammation triggered with non-resorbable microspheres.

In sterile conditions, depyrogenised and sterilized microspheres were suspended in physiological serum. Then, 1 mL sterile syringes were loaded with a volume of microsphere pellet corresponding to 50 mg of dry microspheres. Under general anesthesia, synovial fluid ponction was performed on the right shoulder from 6 adult sheep (3-4 years old), then the syringe containing microspheres was placed on the needle located in the joint cavity. Microspheres were injected slowly in the articular space.

After one and four weeks, animals (3 per group) were sacrificed and synovial fluid from shoulder was recovered. The whole shoulder joints were removed and fixed in formalin 10%. Then, synovial tissues were cut and stained with haematoxylin/eosin for microscopic observation.

In the joint, the injected microspheres were located either into the synovial fluid or in the synovial lining of joint. Migration of microspheres to the synovial lining of capsule did not induce cell proliferation. The inflammatory response of synovial tissue to the resorbable microspheres was compared to inflammation induced by non-resorbable microspheres. Cells surrounding the microspheres incorporated into the synovial lining were numbered (0.1 mm$^2$ field). After one week, 253+/−57 cells were observed around non-resorbable microspheres, whereas only 83+/−15 cells were observed around resorbable microspheres (p<0.0001). One month after injection, 172+/−34 cells surround non-resorbable microspheres compared to 98+/−36 cells for resorbable microspheres (p=0.0005)., The absence of giant cells around the resorbable microspheres confirmed the low level of inflammation induce in joint with these resorbable particles, by opposition to what was observed on non-resorbable microspheres.

In the synovial fluid, at one month after injection, the biodegradable microspheres have disappeared in profit to flat fragments indicating that microsphere resorption had occurred. Concerning the microspheres located within the synovial membrane, they were highly distorted and vacuolized.

Histology showed that resorbable microspheres migrate into the synovial lining and these immobilized microspheres are well tolerated by the synovial tissues of shoulder joint without significant cell proliferation. Furthermore, resorption of microspheres did not induce an inflammatory response.

Example 3

1. Microspheres with a HEMA-PLGA Cross-Linker and a Hydroxyl Function:

A 0.5% of aqueous solution of 88% hydrolyzed polyvinylalcohol (300 ml) was introduced into a 500 ml reactor and allowed to stand under a nitrogen atmosphere for 15 min. The monomer phase containing poly(ethylene glycol)methacrylate (9.45 g; 17.97 mmol), poly(ethylene glycol) methyl ether methacrylate (5.47 g; 18.23 mmol), PLGA cross-linker (0.9 g; 1.52 mmol) and 1 wt % AIBN solubilized in 14 ml of toluene was degassed by bubbling nitrogen through the solution for 15 min. The monomer phase was added to the aqueous phase at 50° C. and agitated by means of a propeller type stirrer at an appropriate velocity so as to obtain monomer droplets of desired diameter. The temperature was increased to 80° C. and stirred for 5 h. The mixture was filtered hot and washed with water and acetone. Then, beads were freeze dry.

2. Microspheres with a HEMA-PLGA Cross-Linker and an Acid Function:

A 0.5% of aqueous solution of 88% hydrolyzed polyvinylalcohol (300 ml) was introduced into a 500 ml reactor and allowed to stand under a nitrogen atmosphere for 15 min. The monomer phase containing methacrylic acid (2.33 g; 27.07 mmol), polyethylene glycol methacrylate (8.05 g; 26.83 mmol), PLGA cross-linker (1.32 g; 2.24 mmol) and 1 wt % AIBN solubilized in 14 ml of toluene was degassed by bubbling nitrogen through the solution for 15 min. The monomer phase was added to the aqueous phase at 50° C. and agitated by means of a propeller type stirrer at an appropriate velocity so as to obtain monomer droplets of desired diameter. The temperature was increased to 80° C. and stirred for 5 h. The mixture was filtered hot and washed with water and acetone. Then, beads were freeze dry.

3. Microspheres with PEG1500-PLGA Cross-Linker and Acid Function:

A solution of Span80® (1%) dissolved in 200 ml of cyclohexane was introduced into a 2000 ml reactor and allowed to stand under a nitrogen atmosphere for 15 min. The monomer phase containing acrylic acid (2.4 g; 33.3 mmol), N,N-dimethylacrylamide (4 g; 40.35 mmol), PEG-PLGA cross-linker (3 g) and 1 wt % ammonium peroxyde disulfate solubilized in 28 ml of water was degassed by bubbling nitrogen through the solution for 15 min. The monomer phase was added to the organic phase at ambient temperature and agitated by means of a propeller type stirrer at an appropriate velocity so as to obtain monomer droplets of desired diameter. The temperature was increased to 70° C. and stirred for 2 h. The mixture was filtered hot and washed with water and acetone. Then, beads were freeze dry.

The invention claimed is:

1. A polymer obtained from the polymerization of:
   (i) at least one monomer of formula (I)

$$(CH_2=CR_1)CO-K \qquad (I)$$

wherein:
   —K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
   —$R_1$, $R_2$, $R_3$, $R_4$ and $R_5$ independently represent H or a C1-C6 alkyl; and
   (ii) at least one bio-resorbable block copolymer cross-linker, wherein the bio-resorbable block copolymer cross-linker is linear and presents $(CH_2=(CR_6))$— groups at both extremities, wherein $R_6$ independently represents H or a C1-C6 alkyl, and wherein the block of the bio-resorbable block copolymer cross-linker is selected from the group consisting of:
   polyethylene glycol (PEG), poly-lactic acid (PLA), poly-glycolic acid (PGA) and poly-lactic-glycolic acid (PLGA), and combinations thereof, wherein the monomer is poly(ethylene glycol) methyl ether methacrylate and wherein the bio-resorbable block copolymer cross-linker is $(CH_2=CCH_3)CO$-PLGA-PEG-PLGA-CO$(CCH_3=CH_2)$.

2. The polymer according to claim 1, which is in the form of a film, a foam, a particle, in particular a spherical particle, a lump, a thread, or a sponge.

3. A pharmaceutical composition comprising at least one polymer in association with a pharmaceutically acceptable carrier, wherein the polymer is obtained from the polymerization of:
   (i) at least one monomer of formula (I)

$$(CH_2=CR_1)CO-K \qquad (I)$$

wherein:
   —K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
   —$R_1$, $R_2$, $R_3$, $R_4$ and $R_5$ independently represent H or a C1-C6 alkyl; and
   (ii) at least one bio-resorbable block copolymer cross-linker, wherein the bio-resorbable block copolymer cross-linker is linear and presents $(CH_2=(CR_6))$— groups at both extremities, wherein $R_6$ independently represents H or a C1-C6 alkyl, and wherein the block of the bio-resorbable block copolymer cross-linker is selected from the group consisting of:
   polyethylene glycol (PEG), poly-lactic acid (PLA), poly-glycolic acid (PGA) and poly-lactic-glycolic acid (PLGA), and combinations thereof,. wherein the monomer is poly(ethylene glycol) methyl ether methacrylate and wherein the bio-resorbable block copolymer cross-linker is $(CH_2=CCH_3)CO$-PLGA-PEG-PLGA-CO$(CCH_3=CH_2)$.

4. An implant comprising a pharmaceutical composition comprising at least one polymer in association with a pharmaceutically acceptable carrier, wherein the polymer is obtained from the polymerization of:
   (i) at least one monomer of formula (I)

$$(CH_2=CR_1)CO-K \qquad (I)$$

wherein:
   —K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
   —$R_1$, $R_2$, $R_3$, $R_4$ and $R_5$ independently represent H or a C1-C6 alkyl; and
   (ii) at least one bio-resorbable block copolymer cross-linker, wherein the bio-resorbable block copolymer cross-linker is linear and presents $(CH_2=(CR_6))$— groups at both extremities, wherein $R_6$ independently represents H or a C1-C6 alkyl, and wherein the block of the bio-resorbable block copolymer cross-linker is selected from the group consisting of:
   polyethylene glycol (PEG), poly-lactic acid (PLA), poly-glycolic acid (PGA) and poly-lactic-glycolic acid (PLGA), and combinations thereof, wherein the monomer is poly(ethylene glycol) methyl ether methacrylate and wherein the bio-resorbable block copolymer cross-linker is $(CH_2=CCH_3)CO$-PLGA-PEG-PLGA-CO$(CCH_3=CH_2)$.

5. An injectable pharmaceutical comprising a pharmaceutical composition comprising at least one polymer in association with a pharmaceutically acceptable carrier, wherein the polymer is obtained from the polymerization of:
   (i) at least one monomer of formula (I)

$$(CH_2=CR_1)CO-K \qquad (I)$$

wherein:
   —K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
   —$R_1$, $R_2$, $R_3$, $R_4$ and $R_5$ independently represent H or a C1-C6 alkyl; and
   (ii) at least one bio-resorbable block copolymer cross-linker, wherein the bio-resorbable block copolymer cross-linker is linear and presents $(CH_2=(CR_6))$— groups at both extremities, wherein $R_6$ independently represents H or a C1-C6 alkyl, and wherein the block of the bio-resorbable block copolymer cross-linker is selected from the group consisting of:
   polyethylene glycol (PEG), poly-lactic acid (PLA), poly-glycolic acid (PGA) and poly-lactic-glycolic acid (PLGA), and combinations thereof, wherein the monomer is poly(ethylene glycol) methyl ether methacrylate and wherein the bio- resorbable block copolymer cross-linker is $(CH_2=CCH_3)CO$-PLGA-PEG-PLGA-CO$(CCH_3=CH_2)$.

6. The implant of claim 4 suitable for implantation into tissues, internal anatomical spaces, body cavities, ducts and vessels.

7. A method for treating a condition selected from the group consisting of inflammation and cancer comprising administering a therapeutically effective amount of a pharmaceutical composition to a patient in need of treatment, wherein the pharmaceutical composition comprises at least one polymer in association with a pharmaceutically acceptable carrier, wherein the polymer is obtained from the polymerization of:

(i) at least one monomer of formula (I)

$$(CH_2=CR_1)CO—K \qquad (I)$$

wherein:
— K represents O—Z or NH—Z, Z representing $(CR_2R_3)_m$—$CH_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
— $R_1$, $R_2$, $R_3$, $R_4$ and $R_5$ independently represent H or a C1-C6 alkyl; and (ii) at least one bio-resorbable block copolymer cross-linker, wherein the bio-resorbable block copolymer cross-linker is linear and presents $(CH_2=(CR_6))$— groups at both extremities, wherein $R_6$ independently represents H or a C1-C6 alkyl, and wherein the block of the bio-resorbable block copolymer cross-linker is selected from the group consisting of:
polyethylene glycol (PEG), poly-lactic acid (PLA), poly-glycolic acid (PGA) and poly-lactic-glycolic acid (PLGA), and combinations thereof, wherein the monomer is poly(ethylene glycol) methyl ether methacrylate and wherein the bio-resorbable block copolymer cross-linker is $(CH_2=CCH_3)CO$-PLGA-PEG-PLGA-CO$(CCH_3=CH_2)$.

8. The pharmaceutical composition according to claim 3, wherein the at least one polymer is in association with a drug or a prodrug.

9. A method for implanting a pharmaceutical composition to a patient in need thereof, comprising implanting an effective amount of the pharmaceutical composition into said patient at a location selected from tissues, internal anatomical spaces, body cavities, ducts and vessels, wherein the pharmaceutical composition comprises at least one polymer in association with a pharmaceutically acceptable carrier, wherein the polymer is obtained from the polymerization of:

(i) at least one monomer of formula (I)

$$(CH_2=CR_1)CO—K \qquad (I)$$

wherein:
— K represents O—Z or NH—Z, Z representing $(CR_2R_3)_m$—$Ch_3$, $(CH_2$—$CH_2$—$O)_m$—H, $(CH_2$—$CH_2$—$O)_m$—$CH_3$, $(CH_2)_m$—$NR_4R_5$ with m representing an integer from 1 to 30;
— $R_1$, $R_2$, $R_3$, $R_4$ and $R_5$ independently represent H or a C1-C6 alkyl; and (ii) at least one bio-resorbable block copolymer cross-linker, wherein the bio-resorbable block copolymer cross-linker is linear and presents $(CH_2=(CR_6))$— groups at both extremities, wherein $R_6$ independently represents H or a C1-C6 alkyl, and wherein the block of the bio-resorbable block copolymer cross-linker is selected from the group consisting of:
polyethylene glycol (PEG), poly-lactic acid (PLA), poly-glycolic acid (PGA) and poly-lactic-glycolic acid (PLGA), and combinations thereof, wherein the monomer is poly(ethylene glycol) methyl ether methacrylate and wherein the bio-resorbable block copolymer cross-linker is $(CH_2=CCH_3)CO$-PLGA-PEG-PLGA-CO$(CCH_3=CH_2)$.

* * * * *